(12) United States Patent
Liu et al.

(10) Patent No.: US 12,133,889 B2
(45) Date of Patent: Nov. 5, 2024

(54) METAL ALUMINUM NANO-ADJUVANT, VACCINE COMPOSITION AND PREPARATION METHOD THEREFOR AND USE THEREOF

(71) Applicant: Jilin University, Jilin (CN)

(72) Inventors: Kun Liu, Changchun (CN); Hua Yu, Changchun (CN); Chenggong Yang, Changchun (CN); Tianmeng Sun, Changchun (CN); Ye Wang, Changchun (CN); Ge Zhu, Changchun (CN)

(73) Assignee: Jilin University, Changchun (CN)

( * ) Notice: Subject to any disclaimer, the term of this patent is extended or adjusted under 35 U.S.C. 154(b) by 88 days.

(21) Appl. No.: 17/728,382

(22) Filed: Apr. 25, 2022

(65) Prior Publication Data
US 2023/0338518 A1 Oct. 26, 2023

(51) Int. Cl.
A61K 39/39 (2006.01)
A61K 9/19 (2006.01)
A61P 35/00 (2006.01)
A61K 39/00 (2006.01)

(52) U.S. Cl.
CPC ............... *A61K 39/39* (2013.01); *A61K 9/19* (2013.01); *A61P 35/00* (2018.01); *A61K 2039/53* (2013.01); *A61K 2039/55505* (2013.01)

(58) Field of Classification Search
CPC ........... A61P 35/00; A61K 39/39; A61K 9/19; A61K 2039/55505; A61K 2039/53
See application file for complete search history.

(56) References Cited

FOREIGN PATENT DOCUMENTS

| CN | 103948921 A | 7/2014 | |
|----|---|---|---|
| CN | 109010810 A | 12/2018 | |
| CN | 109604619 A | 4/2019 | |
| CN | 112704734 * | 4/2021 | ............... A61K 9/19 |
| IN | 202041029290 * | 1/2022 | |
| WO | WO-2019090343 A1 | 5/2019 | |

OTHER PUBLICATIONS

CN112704734 Machine Translation (Year: 2021).*
Erik Lindblad, Aluminum Adjuvants—In Retrospect and Prospect, 22 VACCINE 3658 (Year: 2004).*
Harm HogenEsch, et al, Optimizing the Utilization of Aluminum Adjuvants in Vaccines: You Might Just Get What You Want, 3 NPJ Vaccines 51 (Year: 2018).*
Lingyun Li, et al, Nanoscale Zero-Valent Metals: A Review of Synthesis, Characterization, and Applications to Environmental Remediation, 23 Environ. Sci. Pollut. Res. 17880 (Year: 2016).*
Rostyslav Bilyy, et al, Aluminum Oxide Nanowires as Safe and Effective Adjuvants for Next-Generation Vaccines, 22 Mat. Today 58 (Year: 2019).*
Mar. 27, 2024 First Office Action issued in Chinese Patent Application No. 201911020292.4.
Mar. 27, 2024 Search Report issued in Chinese Patent Application No. 201911020292.4.
Powder metallurgy and technology, Qu Xuanhui, Metallurgical Industry Press, P52, 2013.
Shaoyong Lu et al., "Polymer-Directed Growth of Plasmonic Aluminum Nanocrystals", J. Am. Chem. Soc., 2018, 140, 15412-15418.
Younf-Soon Kwon et. al., "Passivation process for superfine aluminum powders obtained by electrical explosion of wires", Applied Surface Science., 211 (2003) 57-67.
Bingbing Sun et. al., "Enhanced immune adjuvant activity of aluminum oxyhydroxide nanorods through cationic surface functionalization", ACS Appl. Mater. Interfaces, 2017, 9, 21697-21705.
Ping He et al., "Mechanism of aluminum adjuvant and prospect of nanotechnology in it", world Chin J Digestol Nov. 2003; 11(11):1764-1768.
Lanhua Zhao et al., "Efficacy of a New Nano-Emulsion as Influenza Vaccine Adjuvant", Medical Science Journal of Central South China, Sep. 2016, vol. 44, No. 5:575-585.
Haiyan Li, et al., "Alpha-alumina nanoparticles induce efficient autophagy-dependent cross-presentation and potent antitumour response", Natural nanotechnology, 2011(6): 645-650.
Mark T. Orr, et al., "Reprogramming the adjuvant properties of aluminum oxyhydroxide with nanoparticle technology", Nature partner journals, 1 (2019): 1-10.

* cited by examiner

*Primary Examiner* — Sean M Basquill
(74) *Attorney, Agent, or Firm* — Harness, Dickey & Pierce, P.L.C.

(57) ABSTRACT

Disclosed are a metal aluminum nano-adjuvant, a vaccine composition and a preparation method therefor and a use thereof. The vaccine adjuvant comprises metal aluminum nanoparticles, and can be used as a candidate adjuvant for preventive vaccines and therapeutic vaccines for various diseases such as infections, autoimmune diseases and tumors. The combined use of the vaccine adjuvant provided by the present disclosure and antigen can effectively enhance the humoral immune response and the cellular immune response of the vaccine, and the enhancement effect is significantly better than that of the commercially available aluminum hydroxide adjuvant.

18 Claims, 7 Drawing Sheets

Specification includes a Sequence Listing.

METAL ALUMINUM NANO-ADJUVANT, VACCINE COMPOSITION AND PREPARATION METHOD THEREFOR AND USE THEREOF

REFERENCE TO A SEQUENCE LISTING

This application contains references to amino acid sequences and/or nucleic acid sequences which have been submitted concurrently herewith as the sequence listing text file entitled "Sequence Listing.TXT," file size 810 bytes, created on Apr. 25, 2022. The aforementioned sequence listing is hereby incorporated by reference in its entirety pursuant to 37 C.F.R. § 1.52(e)(5).

FIELD

The present disclosure relates to the field of vaccine preparations, in particular to a metal aluminum nano-adjuvant, a vaccine composition and a preparation method therefor and a use thereof.

BACKGROUND

Vaccines are usually used to prevent influenza and other infectious diseases, such as the classic diphtheria vaccine, commonly used influenza vaccine, etc., and vaccine development in recent years is becoming pay attention to treatment from prevention. In addition to treating tumors, the development of therapeutic vaccines also comprises vaccines for lifestyle diseases such as allergy, diabetes and hypertension. Therapeutic vaccines appear in many forms, such as short peptide or protein vaccines, RNA or DNA vaccines, cancer cell vaccines, etc. Although they have undergone several years of clinical trials, most of them have failed to prove effective anticancer effects. One of the important reasons for the ineffectiveness of therapeutic vaccines is that antigens such as short peptides or proteins have low immunogenicity and cannot effectively induce anti-tumor immune responses. Adjuvant is a kind of immune stimulant aimed at enhancing the immune response to vaccines and is widely used in preventive vaccines. With the help of adjuvant, the immune response of antigens such as short peptides or proteins can be effectively improved, and the treatment of diseases such as tumors can be realized. How to improve the specificity of tumor vaccines, regulate the type of immune response, increase the safety and effectiveness of vaccines, and design individualized vaccines have become one of the main research directions at present.

Aluminum salt adjuvant is the most widely used adjuvant in biological products, containing potassium aluminum sulfate, aluminum phosphate and aluminum hydroxide, etc., wherein aluminum hydroxide is used most commonly. Since Glenny first applied aluminum salt to adsorb diphtheria toxoid to have higher antigenicity in 1926, aluminum salt adjuvant has been used as vaccine adjuvant for more than 90 years, and it is the first adjuvant approved by the US Food and Drug Administration (FDA) for human vaccine. At present, the commonly used aluminum hydroxide gel adjuvant is a kind of fibrous particles, which exist in loose form after aggregation, and the particle size is 1-20 Commercial aluminum hydroxide adjuvant is actually the incomplete dehydration product of $Al(OH)_3$, fibrous crystalline aluminum oxyhydroxide AlO(OH). At present, Alhydrogel produced in Denmark is recognized as the standard, and its colloidal particle size is 3.07 μm.

The mechanism of the aluminum salt adjuvant has not yet been fully determined. The existing research results suggest that the possible modes comprise: antigen storage; enhance antigen presentation; enhance humoral immune response mediated by T helper 2 cell (Th2); enhance innate immune response; activate complement, etc. On the other hand, aluminum hydroxide gel adjuvant also has the following shortcomings: the efficiency of inducing cytotoxic T cell immune response is low, and the level of homologous cell reciprocal antibody is often increased, and there are occasionally serious local reactions at the injection site; it may increase the sensitivity of susceptible individuals, and is only suitable as a vaccine antigen adjuvant with strong immunity or can be produced in large quantities.

In recent 20 years, with the rapid development of modern biology, new vaccines such as polypeptide vaccines and recombinant subunit vaccines have emerged, which are equivalent to or more effective than aluminum adjuvant in enhancing immune response. Wherein, nanotechnology provides more new ideas for vaccine research in adjuvant use. Li et al. (J Control Release 2014, 173, 148) immunized mice with vaccines containing nano-aluminum hydroxide adjuvant and conventional micron aluminum hydroxide adjuvant respectively. After 40 days, the tissues of injection sites of mice were observed. The results showed that compared with the conventional aluminum adjuvant, the injection site of the nano-aluminum adjuvant immunized mice had no obvious inflammatory reaction, indicating that the nano aluminum adjuvant had better safety than the conventional aluminum adjuvant. Nanosizing aluminum adjuvants can greatly increase the adjuvant surface area, thereby increasing the antigen adsorption rate. More surprisingly, Sun et al. (Cancer Nanotechnology 2010, 1, 63) found that compared with traditional aluminum hydroxide adjuvant, the tumor size of mice immunized with nano-alumina as an adjuvant was significantly reduced, indicating that nano-alumina adjuvant can improve the antitumor effect of tumor cell vaccine (TCV). Jiang et al. (Adv. Sci. 2018, 5, 1700426) found that the use of nano AlO(OH) particles combined with polymers as an adjuvant effectively improved the cross-presentation of dendritic cells, stimulated the production of CD8+ T cell responses, and also had a good anti-tumor effect. Li et al. (Nat Nanotechnol. 2011, 18, 645) used crystalline $\alpha$-$Al_2O_3$ nanoparticles as an adjuvant, which not only reduced the amount of antigen required to activate T cells, but also induced autophagy-mediated cross-presentation and effective antitumor response.

The preparation methods of metal aluminum nanoparticles can be divided into physical methods and chemical methods. Physical methods mainly comprise ball milling, electric explosion, photolithography, vapor evaporation, etc. Generally speaking, although the aluminum particles prepared by electron beam photolithography technology have uniform particle size and good purity, it is only suitable for a small amount of preparation at present, and the requirements for instruments are high and the equipment is complex. The principle of electric explosion is that a strong current is applied to metal wire or metal foil, the heating effect of resistance will make considerable energy accumulate rapidly in the wire or foil, which will cause phase change, accompanied by explosion and flash, and at the same time an evaporation area containing metal particles with a particle size of about 100 nm was formed, and nanoparticles after condensation was formed. The advantages of the electric explosion method are large production capacity and high product quality.

Because aluminum compounds are difficult to be reduced by general reducing agents, metal aluminum is easily oxidized, and the environment for synthesizing metal aluminum needs to be strictly anhydrous and oxygen-free, so the chemical synthesis of aluminum nanoparticles is quite challenging. At present, thermal decomposition and catalytic decomposition are mostly concentrated. In 1998, Haber et al. (J. Am. Chem. Soc. 1998, 120, 10847) used the complex formed by N,N-dimethylethylamine and aluminum hydride as the precursor and titanium propoxide as the catalyst to reflux in 1,3,5-trimethylbenzene to obtain nano-sized aluminum with an average size of 40-180 nm, and the aggregation degree of the particles mainly depends on the amount of catalyst. In 2009, Meziani et al. (ACS Appl. Mater. Interfaces 2009, 1, 703) used 1-methylpyrrole and N,N-dimethylethylamine to form complexes with aluminum hydride as precursors, respectively, used molecules with carboxylic acid functional groups as ligands to stabilize the particle surface, and aluminum nanoparticles with clear boundaries and good dispersibility were prepared. In 2015, McClain et al. (Nano Lett. 2015, 15, 2751) used oleic acid as ligand, and preliminarily controlled the size of aluminum nanocrystals by adjusting the ratio of tetrahydrofuran and 1,4-dioxane, and 70-220 nm high-purity dispersed aluminum nanoparticles were synthesized. Due to the lack of suitable ligands to stabilize the particle surface, the particle size distribution is uneven and the morphology is difficult to control. In 2018, Lu Shaoyong et al. (J. Am. Chem. Soc. 2018, 146, 15412) first selected dithioester-terminated polystyrene (CDTB-PS) as the ligand to control the nucleation and growth process of aluminum particles and aluminum particle solutions with different colors were synthesized. By changing the amount of catalyst and adjusting the number of nucleation particles, the controllable synthesis of aluminum nanoparticles with a size of 90-250 nm and good monodispersity can be realized.

Therefore, under the premise that the effectiveness and safety of aluminum salt adjuvant are recognized, it is a technical problem to be solved urgently in the art to the modify aluminum adjuvant, further improve the body's immune response to antigen, improve the efficiency of inducing cytotoxic T cell immune response, and enhance its antigenic storage effect and enhance or improve the immune stimulation effect, thereby improving its adjuvant effect.

SUMMARY

The technical problem to be solved in the present disclosure is to overcome the defect of low induction efficiency of cellular immune response of traditional aluminum salt adjuvants (such as aluminum hydroxide, aluminum phosphate, etc.), and the present disclosure provides a metal aluminum nano-adjuvant, a vaccine composition and a preparation method therefor and a use thereof. The metal aluminum nano-adjuvant provided by the present disclosure has controllable size, monodisperse particle size (dispersion coefficient≤0.15) and stable colloid, and can be used as candidate adjuvant for preventive vaccine and therapeutic vaccine for various diseases such as infections, autoimmune diseases and tumors. The combined use of the vaccine adjuvant and the antigen provided by the present disclosure can effectively enhance the humoral immune response and the cellular immune response of the vaccine, and the enhancement effect is significantly better than that of the commercially available aluminum hydroxide adjuvant.

The present disclosure provides a vaccine adjuvant, comprising metal aluminum nanoparticles.

In the present disclosure, the metal aluminum nanoparticles can be conventional metal aluminum particles with nanometer particle size (particle size≤1000 nm) in the art, and generally have an amorphous alumina layer with a thickness of 3-5 nm on the surface.

In the present disclosure, the average particle size of the metal aluminum nanoparticles is preferably 10-999 nm, more preferably 50-300 nm; such as 88.85 nm±8.86 nm, 147.14 nm±11.95 nm, 139.76±42.81 nm or 287.82 nm±24.13 nm.

In the present disclosure, the metal aluminum nanoparticles are preferably metal aluminum nanoparticles with a dispersion coefficient of circumscribed circle diameter≤0.21, such as metal aluminum nanoparticles with a dispersion coefficient of 0.09, a dispersion coefficient of 0.08, or a dispersion coefficient of 0.10.

In the present disclosure, preferably, the average particle size and dispersion coefficient of the metal aluminum nanoparticles are as follows: 88.85 nm±8.86 nm, the dispersion coefficient is 0.10; 147.14 nm±11.95 nm, the dispersion coefficient is 0.09; or, 287.82 nm±24.13 nm, the dispersion coefficient is 0.08.

In the present disclosure, the metal aluminum nanoparticles are preferably metal aluminum nanoparticles with controllable size, monodisperse particle size (dispersion coefficient≤0.15), and stable colloid. Generally, the particle size of metal aluminum nanoparticles can be observed and measured by electron microscope, so as to obtain the metal aluminum nanoparticles with controllable size, monodisperse particle size and stable colloid.

In the present disclosure, the metal aluminum nanoparticles can be prepared according to conventional methods in the art, such as electric explosion method or ligand regulation method.

Wherein, the electric explosion method can be carried out according to conventional methods in the art, for example, in an inert environment, vaporizing the aluminum wire by electric current to form aluminum vapor, and after condensation, obtaining the metal aluminum nanoparticles.

The inert environment can be an argon environment.

The current conditions can be: the power supply capacitance is 96 μF, and the electrode discharge voltage is 4.0-4.4 kV.

The aluminum wire can be a conventional aluminum wire in the art, such as an aluminum wire with a diameter of 0.2 mm and a purity of 95%.

Wherein, the ligand regulation method can be carried out according to conventional methods in the art, preferably, the ligand regulation method comprises the following steps: in an atmosphere with a water content lower than 10 ppm and an oxygen content lower than 100 ppm, in the presence of titanium catalyst, reacting the ligand solution with the precursor solution;

the ligand is a polymer with a functional group containing sulfur atom as a terminal group, and the polymerization degree of the ligand is 10-1000; the structural formula of the precursor is $H_3Al-X$, and the X is an organic molecule, and the organic molecule contains atoms that are able to coordinate with aluminum and have lone pair electrons.

In the ligand regulation method, the atmosphere with extremely low water content and oxygen content can be obtained by conventional methods in the art of chemistry, for example, obtained through a glove box. The water content is preferably lower than 1 ppm. The oxygen content is preferably lower than 50 ppm, more preferably lower than 1 ppm.

In the ligand regulation method, the titanium catalyst can be an organotitanium catalyst conventionally used in the art for such reactions and can be dissolved in a reaction solvent, preferably titanium tetraisopropanolate (Ti(i-PrO)$_4$).

In the ligand regulation method, the ligand is preferably

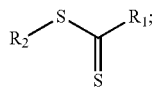

wherein: $R^1$ is $C_{1-10}$ alkyl, $C_{6-30}$ aryl, or $C_{6-30}$ aryl substituted by $R^{1a}$; $R^2$ is

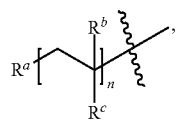

and $R^a$ is $C_{1-10}$ alkyl, or $C_{1-10}$ alkyl substituted by $R^{a1}$, and $R^{a1}$ is $C_{6-30}$ aryl; $R^b$ is H or $C_{1-10}$ alkyl; $R^c$ is $C_{6-30}$ aryl, $C_{6-30}$ aryl substituted by $R^{c1}$, or

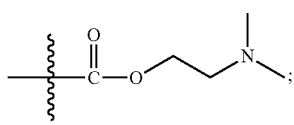 [SMILES: *C(=O)OCCN(C)C]

$R^{1a}$ and $R^{c1}$ are each independently $C_{1-10}$ alkyl or halogen.

When $R^1$ is $C_{1-10}$ alkyl, the $C_{1-10}$ alkyl is preferably $C_{1-6}$ alkyl, more preferably $C_{1-3}$ alkyl, such as methyl or isopropyl.

When $R^{1a}$ is $C_{1-10}$ alkyl, the $C_{1-10}$ alkyl is preferably $C_{1-6}$ alkyl, more preferably $C_{1-3}$ alkyl, such as methyl or isopropyl.

When $R^a$ is $C_{1-10}$ alkyl, or $C_{1-10}$ alkyl substituted by $R^{a1}$, the $C_{1-10}$ alkyl is preferably $C_{1-6}$ alkyl, more preferably $C_{1-3}$ alkyl, such as methyl or isopropyl.

When $R^b$ is $C_{1-10}$ alkyl, the $C_{1-10}$ alkyl is preferably $C_{1-6}$ alkyl, more preferably $C_{1-3}$ alkyl, such as methyl or isopropyl.

When $R^1$ is $C_{6-30}$ aryl, or $C_{6-30}$ aryl substituted by Ria, the $C_{6-30}$ aryl is preferably $C_{6-10}$ aryl, more preferably phenyl.

When $R^{a1}$ is $C_{6-30}$ aryl, the $C_{6-30}$ aryl is preferably $C_{6-10}$ aryl, more preferably phenyl.

When $R^c$ is $C_{6-30}$ aryl, or $C_{6-30}$ aryl substituted by $R^{c1}$, the $C_{6-30}$ aryl is preferably $C_{6-10}$ aryl, more preferably phenyl.

When $R^{1a}$ and/or $R^{c1}$ are halogen, the halogen is preferably Br or Cl.

The $C_{1-10}$ alkyl substituted by $R^{a1}$ is preferably $C_{1-3}$ alkyl substituted by phenyl, more preferably

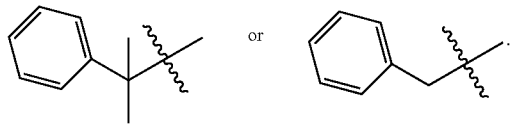

In the ligand regulation method, the polymerization degree of the ligand is preferably 20-1000, more preferably 40-240, such as 42.

In the ligand regulation method, the PDI of the ligand is preferably 1-2, more preferably 1-1.51, such as 1.09.

In the ligand regulation method, the structural formula of the ligand can be shown in formula (1), wherein Mn is 4.5 kg/mol, n is 42, and PDI is 1.09. The preparation method can be a conventional preparation method in the art, preferably reacting styrene, 2,2'-azobis(2-methylpropionitrile) and 2-phenyl-2-propyl benzodithioate under anhydrous and oxygen-free conditions, for example, the ligand can be synthesized with reference to the following document: Journal of Polymer Science Part A: Polymer Chemistry 2001, 39, 1553.

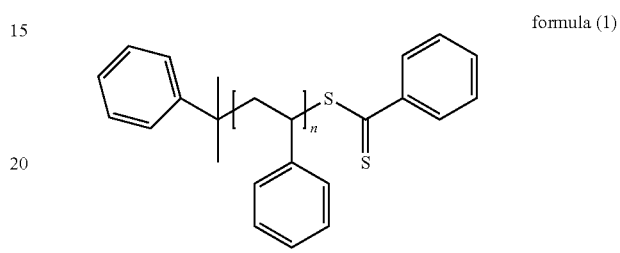

formula (1)

In the ligand regulation method, in the precursor, X is preferably an organic molecule containing N or O atoms, more preferably tertiary amine (NR$_3$) or tetrahydrofuran, such as Preferably, the precursor is When the precursor is the preparation method preferably comprises: adding 1-methylpyrrolidine dropwise to a toluene solution of lithium aluminum hydride and aluminum chloride to carry out the reaction.

Both oxygen and water contents generally keep lower than 1 ppm during the preparation process of the precursor for example, the preparation process can be carried out in a glove box.

In the preparation process of the precursor

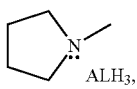

the mass concentration of the lithium aluminum hydride in the toluene solution of the lithium aluminum hydride and aluminum chloride can be a conventional mass concentration in the art, preferably 20-1000 mg/mL, more preferably 20-200 mg/mL, such as 83.3 mg/mL. In the toluene solution of the lithium aluminum hydride and aluminum chloride, the mass concentration of the aluminum chloride can be a conventional mass concentration in the art, preferably 10-1000 mg/mL, more preferably 10-200 mg/mL, such as 91.8 mg/mL.

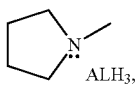

In the preparation process of the precursor the molar ratio of the lithium aluminum hydride, the aluminum chloride and the 1-methylpyrrolidine can be a conventional molar ratio in the art, preferably (2-4):1:(0.8-1.5), more preferably 3:1:1.

In the preparation process of the precursor

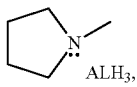

the parameters and conditions of the reaction can be conventional parameters and conditions in the art. The temperature of the reaction is generally room temperature, such as 20-30° C. The reaction time can be conventional in the art, preferably 2-24 hours, such as 12 hours. In the reaction process, the stirring speed can be conventional in the art, preferably 300-1000 rpm, more preferably 800 rpm.

In the preparation process of the precursor

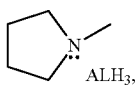

the reaction solution obtained by the reaction is preferably subjected to post-treatment. The operations and conditions of the post-treatment are all conventional in the art, and generally filtration is sufficient, preferably, removing impurities by funnel filtration first, and then filtering the obtained filtrate through an organic phase filter membrane. The pore size of the organic phase filter membrane can be conventional in the art, preferably 0.01-1 μm, such as 0.22 μm. The material of the organic phase filter membrane can be an organic material conventionally used as a filter membrane in the art. Generally, the precursor is stored in the refrigerator of glove box at a low temperature, and the store temperature is −10° C.

In the ligand regulation method, in the reaction solution, the concentration of the precursor is preferably 15-500 mM, more preferably 20-100 mM, such as 50 mM or 80 mM.

When the concentration of the precursor is 15-100 mM, the concentration of the titanium catalyst is preferably 0.1-1.5 mM; for example, when the concentration of the precursor is 80 mM, the concentration of the titanium catalyst is 0.2 mM.

In the ligand regulation method, the concentration of the ligand solution can be a conventional concentration in the art, preferably, the molar ratio of the ligand to the precursor is 3:(500-800), such as 3:800.

In the ligand regulation method, the concentration of the titanium catalyst solution can be a conventional concentration in the art, and preferably, the molar ratio of the titanium catalyst to the precursor is 1:(350-550), such as 1:400.

In the ligand regulation method, the molar ratio of the ligand, the precursor and the titanium catalyst can be a conventional molar ratio in the art, preferably 1:(60-520):(0.04-1.6), more preferably 1:(70-500):(0.05-1.5), such as 3:800:2.

In the ligand regulation method, the solvent in the ligand solution and the precursor solution can be a conventional solvent in the art, preferably an aprotic solvent, more preferably one or more of toluene, tetrahydrofuran and ether solvents. In the aprotic solvent, the oxygen content is preferably lower than 10 ppm, and the water content is preferably lower than 10 ppm.

In the ligand modulation method, the reaction is preferably carried out in a glove box.

In the ligand regulation method, the operations and conditions of the reaction can be conventional operations and conditions in the art. The reaction time is preferably 10 minutes to 24 hours, such as 45 minutes, 1.5 hours or 4 hours. The temperature of the reaction is generally from room temperature to the boiling point of the selected solvent in the reaction solution. For example, when the solvent in the reaction solution is tetrahydrofuran, the temperature of the reaction is preferably 40-60° C., more preferably 50° C.

In the ligand regulation method, the operation of the reaction is preferably carried out according to the following steps: in the ligand solution, adding the precursor solution and the titanium catalyst solution successively to carry out the reaction.

In the ligand regulation method, the reaction is preferably carried out under stirring conditions, wherein the stirring speed can be 50-3000 rpm, preferably 500 rpm.

In the ligand regulation method, the reaction solution obtained from the reaction can be subjected to post-treatment according to conventional operations and conditions in the art, for example, after cooling to room temperature, removing the supernatant by centrifugation, and washing. The conditions of the centrifugation can be 8000 rpm centrifugation for 10 minutes. The washing conditions can be as follows: adding the solvent used in the reaction solution and shaking, and washing the precipitate, and circulating for three times.

The present disclosure also provides a preparation method of the vaccine adjuvant, comprising the following steps: mixing the metal aluminum nanoparticles and solvent A to prepare a vaccine adjuvant suspension.

Wherein, the solvent A can be a conventional solvent in the art that can disperse metal aluminum nanoparticles and does not dissolve metal aluminum nanoparticles, preferably one or more of alcohol solvents, ether solvents, ketone solvents, dimethyl sulfoxide, NN-dimethylformamide (DMF) and tetrahydrofuran, more preferably N,N-dimethylformamide. The alcohol solvent is preferably methanol and/or ethanol.

Wherein, in the vaccine adjuvant suspension, the concentration of the metal aluminum nanoparticles is preferably 0.1-100 mg/mL, more preferably 0.1-20 mg/mL, further preferably 0.1-5 mg/mL, such as 2 mg/mL.

Wherein, the mixing method can be a conventional mixing method in the art, such as ultrasonic dispersion. The ultrasonic dispersion time can be 10-120 min, such as 20 min.

In the present disclosure, the vaccine adjuvant can not only induce humoral immunity, but also stimulate cellular immune response.

The present disclosure also provides a vaccine composition, comprising the vaccine adjuvant, and an antigen or DNA encoding the antigen.

In the present disclosure, the antigen can be a conventional substance in the art that can stimulate the body to produce a specific immune response, or it can be alone can not induce immune response, but when it is cross-linked or combined with a carrier such as macromolecular protein or a non-antigenic polylysine, then a small molecule substance (also known as hapten) with immunogenicity can be obtained. The antigen can be one or more of short peptides, polypeptides and proteins.

Wherein, the short peptide can be a conventional short peptide in the art, generally refers to a short chain peptide composed of 3-9 amino acid residues, such as antigen peptide OT-1 of ovalbumin OVA, antigenic glycoprotein gp100 of melanoma cells or apoptosis inhibitory protein survivin/birc5-1.

Sequence of the antigenic peptide OT-1 can be SIINFEKL (SEQ ID NO: 1).

Molecular weight of the antigenic peptide OT-1 can be 963.14 g/mol.

Wherein, the polypeptide can be a conventional polypeptide in the art, generally refers to a compound formed by dehydration condensation of 10-100 amino acid molecules, such as telomerase activity catalytic unit TERT, or, "T cell recognition melanoma antigen MART-1, MOG35-55, PADRE, Trp2 or survivin/birc5-2".

Sequence of the telomerase activity catalytic unit TERT can be DLQPYMGQFLKHLQDSDASALRNSVVI (SEQ ID NO: 2).

Molecular weight of the telomerase activity catalytic unit TERT can be 3046.70 g/mol.

Wherein, the protein can be a conventional protein in the art, generally refers to a substance with a certain spatial structure formed by the coiling and folding of a polypeptide chain composed of amino acids in the manner of "dehydration condensation", such as ovalbumin OVA.

Molecular weight of the OVA can be 298.4 g/mol.

In the present disclosure, the mass ratio of the metal aluminum nanoparticles to the antigen is preferably 2:(0.1-10), such as 2:(1-3), and further such as 2:3 or 1:1.

When the antigen is a short peptide and/or polypeptide, the mass ratio of the metal aluminum nanoparticles to the antigen is preferably 1:1.

When the antigen is a protein, the mass ratio of the metal aluminum nanoparticles to the antigen is preferably 2:3.

The present disclosure also provides a preparation method of vaccine composition, comprising the following steps: mixing the vaccine adjuvant with a solution containing the antigen, and carrying out an incubation reaction.

In the present disclosure, the solution containing the antigen can be prepared by a conventional method in the art, for example, mixing the antigen with solvent B.

Wherein, the solvent B can be a conventional solvent in the art that can be used for dissolving antigens, preferably water, PBS buffer, DMF or alcohol solvent, more preferably PBS buffer or DMF.

In the present disclosure, in the solution containing the antigen, the concentration of the antigen is preferably 0.01-10 mg/mL, more preferably 0.1-5 mg/mL, such as 2.0 mg/mL or 3.0 mg/mL.

When the vaccine adjuvant in the form of the vaccine adjuvant suspension is mixed with the solution containing the antigen, preferably, the solvent A and the solvent B are soluble.

Wherein, preferably, when the antigen is the short peptide and/or polypeptide, the solvent A and the solvent B are the same; for example, the solvent A is DMF, and the solvent B is DMF.

Wherein, preferably, when the antigen is the protein, the solvent A and the solvent B are different; for example, the solvent A is DMF, and the solvent B is PBS buffer.

Wherein, preferably, adding the solution containing the antigen to the vaccine adjuvant suspension, and after ultrasonic dispersion, carrying out the incubation reaction. This mixing sequence can make antigen coating more uniform.

In the present disclosure, the operations and conditions of the incubation reaction can be conventional operations and conditions in the art, for example, carrying out ultrasonic dispersion first, followed by incubation. The ultrasonic dispersion time can be 5-120 min, such as 10-120 min, preferably 30 min.

In the present disclosure, the incubation reaction can be carried out in a shaker.

In the present disclosure, preferably, the incubation reaction is carried out under the condition of 80-800 rpm, preferably 240-320 rpm, such as 320 rpm.

In the present disclosure, the time of the incubation reaction can be 1-24 hours, such as 12 hours.

In the present disclosure, the temperature of the incubation reaction is generally room temperature, such as 20-30° C.

In the present disclosure, after the incubation reaction, the vaccine composition can also be centrifuged to remove supernatant according to conventional operations in the art.

Wherein, the operations and conditions of the centrifugation can be conventional operations and conditions in the art. The speed of the centrifugation is preferably 3000-15000 rpm, more preferably 5000-15000 rpm, such as 6000 rpm or 12000 rpm. The centrifugation time is preferably 5-20 min, such as 10 min.

The present disclosure also provides a lyophilized vaccine, comprising the metal aluminum nanoparticles and the antigen.

Wherein, preferably, the lyophilized vaccine is prepared by the following method: mixing the vaccine composition with water and lyophilizing.

The present disclosure also provides a use of the metal aluminum nanoparticles as a vaccine adjuvant in a vaccine.

Wherein, the metal aluminum nanoparticles are described as above.

The above preferred conditions of the present disclosure may be arbitrarily combined based on the general knowledge in the art to obtain the preferred embodiments of the present disclosure.

The reagents and raw materials used in the present disclosure are all commercially available.

The positive progress effects of the present disclosure are:

(1) The present disclosure provides a vaccine adjuvant prepared by using metal aluminum nanoparticles as raw material. The combined use of the vaccine adjuvant and the antigen can effectively enhance the humoral immune response and the cellular immune response of the vaccine, and the enhancement effect is significantly better than that of the commercially available aluminum hydroxide adjuvant.

(2) The metal aluminum nano-adjuvant in the present disclosure has good stability and good safety, and can be used as a candidate adjuvant for preventive vaccine and therapeutic vaccine against infections, autoimmune diseases, tumors and other diseases.

DETAILED DESCRIPTION

Figure 1:
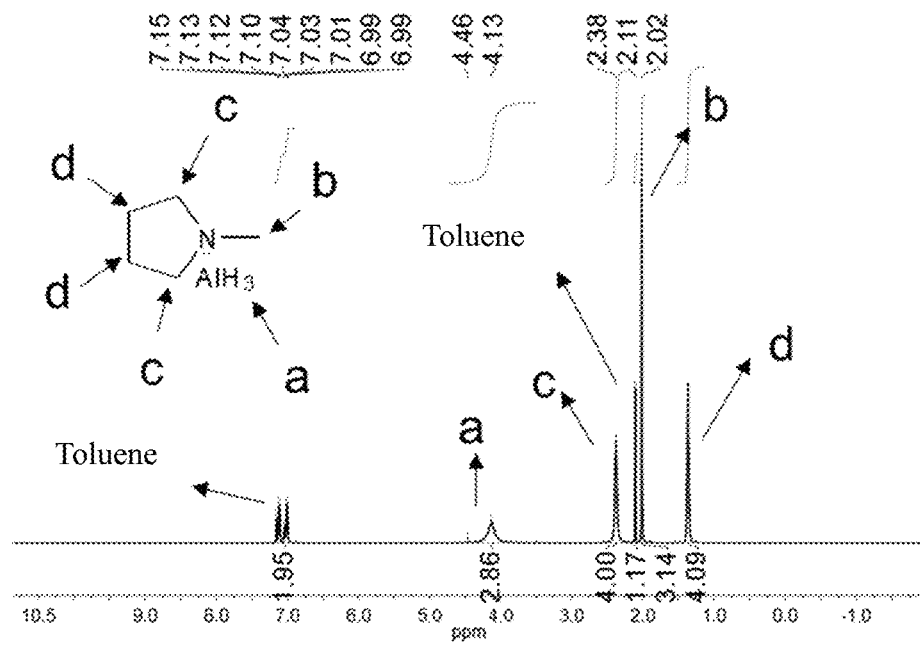
FIG. 1 is the 1H nuclear magnetic resonance spectrum (deuterated benzene) of the precursor $H_3Al$ (1-MP) of Embodiment 2.

The following embodiments further illustrate the present disclosure, but the present disclosure is not limited thereto. The experimental methods without specific conditions in the following embodiments are selected according to conventional methods and conditions, or according to the product description.

In the following embodiments and comparative embodiments:

Ovalbumin OVA was purchased from sigma-aldrich, molecular weight was 298.4 g/mol;

short peptides or polypeptides were purchased from Gill Biochemical (Shanghai) Co., Ltd. The specific information was as follows:

polypeptide Tert (DI-27): sequence was DLQPYIVIGQFLKHLQDSDASALRN SVVI (SEQ ID NO: 2), molecular weight was 3046.70 g/mol;

short peptide OT-1: sequence was SIINFEKL (SEQ ID NO: 1), molecular weight was 963.14 g/mol.

Embodiment 1 Preparation of Metal Aluminum Nanoparticles by Electric Explosion Method In argon atmosphere, an aluminum wire with a diameter of 0.2 mm and a purity greater than or equal to 95% was fixed between the high-voltage electrodes, continuously powered by a mechanical device, and the power supply capacitance was 96 μF, and the electrode discharge voltage was 4.0-4.4 kV. Under a high-density current, the aluminum wire was heated and radially expanded to be vaporized to form aluminum vapor, and then condensed to form aluminum particles with an average particle size of 139.76±42.81 nm, then aluminum particles were collected in an argon-filled collector. (See document: Passivation Process for Superfine Aluminum Powders Obtained by Electrical Explosion of Wires. Appl. Sur. Sci. 2003, 211, 57-67.)

Embodiment 2 Preparation of Metal Aluminum Nanoparticles by Ligand Regulation Method (1) Synthesis and Characterization of Precursor $H_3Al$ (1-MP)

In a glove box (both oxygen and water content were lower than 1 ppm), 3.748 g of lithium aluminum hydride and 4.132 g of aluminum chloride were added to a flask containing 45 mL of anhydrous toluene. Under strong stirring (the stirring speed was 800 rpm), 11.65 mL of 1-methylpyrrolidine was added dropwise. Wherein, the molar ratio of lithium aluminum hydride, aluminum chloride, and 1-methylpyrrolidine was 3:1:1. After the reaction was carried out overnight at room temperature, the reaction mixture was filtered with a funnel to remove solid impurities. For further purification, the obtained filtrate was filtered again with an organic phase filter membrane with a pore size of 0.22 μm, and the obtained filtrate was a toluene solution of $H_3Al$ (1-MP) (structural formula was

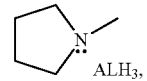

the yield was 90%), and the solution was then stored in a glove box refrigerator at low temperature; the storage temperature was −10° C. The concentration of the solution can be calibrated by 1H nuclear magnetic resonance spectrum.

FIG. 1 is the 1H nuclear magnetic resonance spectrum (deuterated benzene) of the precursor $H_3Al$ (1-MP) of Embodiment 2. $^1$NMR ($C_6D_6$): δ4.13 (s, br, 3H, $H_3Al$), 2.38 (s, 4H, N($CH_2CH_2$)$_2$), 2.02 (s, 3H, $NCH_3$), 1.37 (m, 4H, N($CH_2CH_2$)$_2$); $^{27}$Al NMR ($C_6D_6$): δ 140.87 (s, br).

Figure 2:
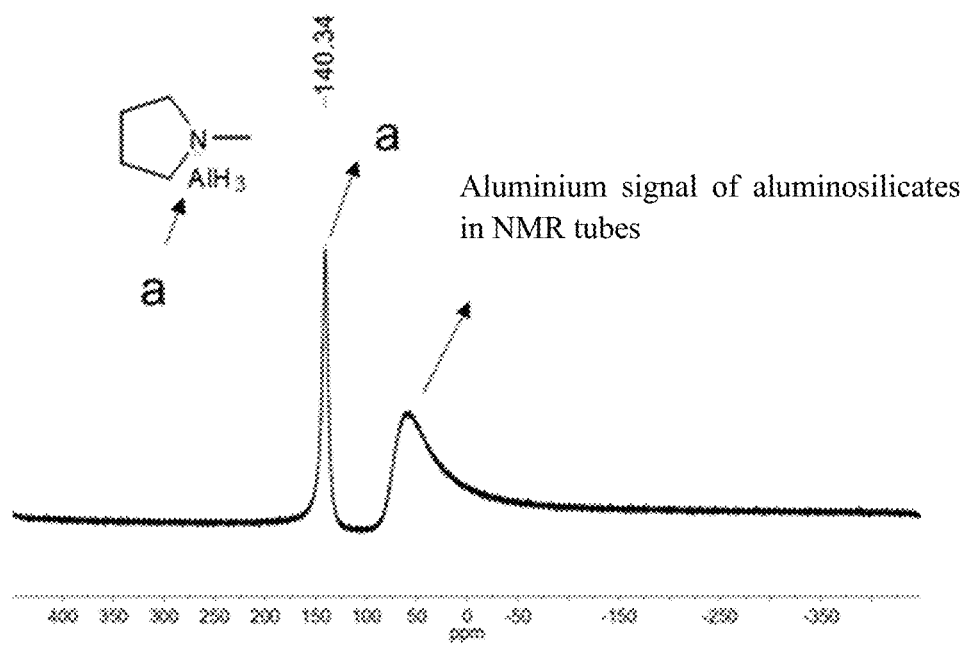
FIG. 2 is the 27Al nuclear magnetic resonance spectrum (deuterated benzene) of the precursor $H_3Al$ (1-MP) of Embodiment 2.

FIG. 2 is the 27Al nuclear magnetic resonance spectrum (deuterated benzene) of the precursor $H_3Al$ (1-MP) of Embodiment 2. $^{27}$Al NMR ($C_6D_6$): δ140.87 (s, br).

(2) Synthesis and characterization of ligand (2-phenyl-2-propyl benzodithioate)-terminated polystyrene (CDTB-PS)

90.90 g of styrene, 0.0576 g of 2,2'-azobis(2-methylpropionitrile), and 0.4107 g of 2-phenyl-2-propyl benzodithioate (CDTB) were added to the Schelenk flask. After three times of liquid nitrogen freezing-vacuumizing-melting treatment, the mixed solution was reacted in an oil bath at 60° C. for 12 hours under stirring, and then the reaction solution was cooled to room temperature. Then, most of the unreacted styrene was removed with a rotary evaporator. Finally, the reaction solution was washed by sedimentation with methanol-ultrasonic centrifugation three times to remove the reactant. The product was placed in a vacuum oven at 120° C. for 1 day, and the final solid product was stored in a glove box refrigerator at low temperature. The molecular weight (Mn) of the product was about 4.5 kg/mol, and the dispersion index (PDI) was 1.09. 7.64 g of the product was obtained with a yield of 8.5%. The structure of the product was as follows:

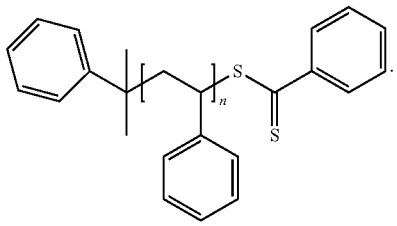

(n is 42)

Figure 3:
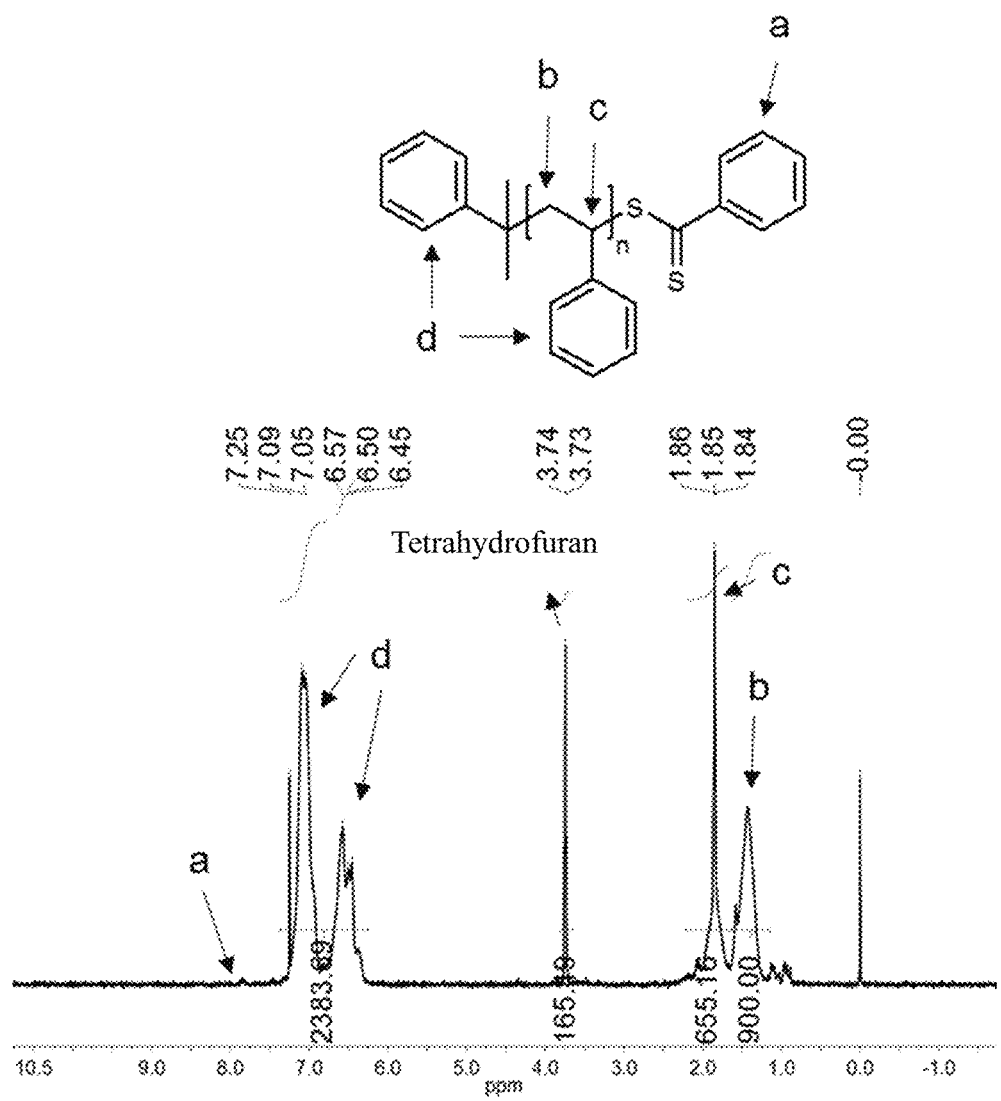
FIG. 3 is the 1H nuclear magnetic resonance spectrum (deuterated chloroform) of ligand (2-phenyl-2-propyl benzodithioate)-terminated polystyrene (CDTB-PS) of Embodiment 2.

FIG. 3 is the 1H nuclear magnetic resonance spectrum (deuterated chloroform) of ligand (2-phenyl-2-propyl benzodithioate)-terminated polystyrene (CDTB-PS) of Embodiment 2. 1H NMR: CDTB-PS (Mn=4.5 kg/mol) (CDCl$_3$): δ7.85 (br, —S—CS—C$_6$H$_5$), 6.37-7.31 (br, 5H, Ph), 1.85 (br, 1H, CHCH$_2$), 1.37 (br, 2H, CHCH$_2$).

Figure 4:
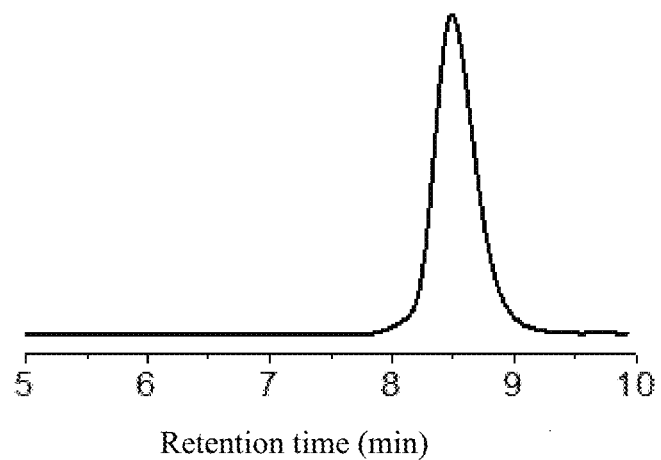
FIG. 4 is gel permeation chromatogram (GPC) of ligand (2-phenyl-2-propyl benzodithioate)-terminated polystyrene (CDTB-PS) of Embodiment 2.

FIG. 4 is gel permeation chromatogram (GPC) of ligand (2-phenyl-2-propyl benzodithioate)-terminated polystyrene (CDTB-PS) of Embodiment 2.

(3) Synthesis and Characterization of Aluminum Nanoparticles

Preparation of the Solution:

An anhydrous THF solution of CDTB-PS with a concentration of 20 mM was prepared, and a little excess CDTB-PS was added roughly according to the molecular weight, and the accurate concentration was calibrated by ultraviolet quantitative method.

An anhydrous THF solution of H$_3$Al (1-MP) with a concentration of 1M was prepared. The specific preparation method was as follows: the concentration of H$_3$Al (1-MP) solution (usually greater than 1M) was determined according to the integral area relationship of specific peak of liquid $^1$H NMR. By calculation, the anhydrous THF solution of H$_3$Al(1-MP) with a concentration of 1M was obtained by adding a specific volume of THF.

An anhydrous THF solution of Ti(i-PrO)$_4$ with a concentration of 100 mM was prepared. The mass of Ti(i-PrO)$_4$ was weighed with a balance and a specific volume of THF was added.

In a glove box (both oxygen and water content were lower than 1 ppm), 75 μL of a solution of 20 mM CDTB-PS in anhydrous THF was added to 4.425 mL of anhydrous tetrahydrofuran (THF), and the reaction solution was heated and stabilizing to 50° C. Under strong stirring (500 rpm), 400 μL of a solution of 1M H$_3$Al(1-MP) in anhydrous THF and 100 μL of a solution of 10 mM Ti(i-PrO)$_4$ in anhydrous THF were added successively. Wherein, the molar ratio of ligand, precursor and Ti(i-PrO)$_4$ was 3:800:2; after the feeding was completed, in the whole reaction solution (solvent 5.0 mL), the concentration of H$_3$Al(1-MP) precursor was 80 mM, the concentration of titanium catalyst was 0.2 mM. The reaction was carried out at 50° C. under strong stirring (500 rpm), and the reaction solution was cooled to room temperature at 45 minutes, 1.5 hours, and 4 hours, respectively; the reaction solution was centrifuged at 8000 rpm for 10 minutes. The supernatant was removed, and an equal amount of anhydrous THF was added, then the precipitate was washed by shaking. After repeating three times, aluminum nanoparticles with good monodispersity with a size of 88.85 nm±8.86 nm and a dispersion coefficient of 0.10; a size of 147.14 nm±11.95 nm and a dispersion coefficient of 0.09; a size of 287.82 nm±24.13 nm and a dispersion coefficient of 0.08 were obtained respectively.

Embodiment 3

The vaccine AlNPs-OVA was prepared by mixing metal aluminum nanoparticles obtained by electric explosion with OVA. Specific steps were as follows:
(1) The metal aluminum nanoparticles obtained by electric explosion and prepared in Embodiment 1 were prepared into a solution of 0.1-5.0 mg/mL (using DMF as solvent), and the concentration of the metal aluminum nanoparticles in the present embodiment was 2.0 mg/mL, and ultrasonic dispersion was performed for 20 minutes.
(2) Ovalbumin OVA PBS solution with a concentration of 0.1-5.0 mg/mL was prepared. In the present embodiment, the concentration of ovalbumin OVA was 3.0 mg/mL.
(3) A PBS solution of ovalbumin OVA and a DMF solution of aluminum nanoparticles were mixed according to the volume of 1:1, after ultrasonic dispersion for half an hour, the reaction solution was transferred to a shaker, and shaked at room temperature at 320 rpm for 12 hours. After stopping shaking, the reaction solution was centrifuged at 12,000 rpm for 10 minutes, and the supernatant was removed and the samples was lyophilized to remove the remaining small amount of solvent.

Embodiment 4

The vaccine 287.82 nm Al-OVA was prepared by mixing 287.82 nm metal aluminum nanoparticles with OVA. Specific steps were as follows:

The aluminum particles with a size of 287.82 nm±24.13 nm and a dispersion coefficient of 0.08 prepared in Embodiment 2 were used, and the remaining steps were the same as those in Embodiment 3.

Embodiment 5

The vaccine 147.14 nm Al-OVA was prepared by mixing 147.14 nm metal aluminum nanoparticles with OVA. Specific steps were as follows:

The aluminum particles with a size of 147.14 nm±11.95 nm and a dispersion coefficient of 0.09 prepared in Embodiment 2 were used, and the remaining steps were the same as those in Embodiment 3.

Embodiment 6

The vaccine 88.85 nm Al-OVA was prepared by mixing 88.85 nm metal aluminum nanoparticles with OVA. Specific steps were as follows:

The aluminum particles with a size of 88.85 nm±8.86 nm and a dispersion coefficient of 0.10 prepared in Embodiment 2 were used, and the remaining steps were the same as those in Embodiment 3.

Embodiment 7

The vaccine 147.14 nm Al-OT-1 was prepared by mixing 147.14 nm metal aluminum nanoparticles with short peptide OT-1. Specific steps were as follows:
(1) The metal aluminum nanoparticles with a size of 147.14 nm±11.95 nm and a dispersion coefficient of 0.09 prepared in Embodiment 2 were prepared into a solution of 0.1-5.0 mg/mL (using DMF as solvent), and the concentration of the metal aluminum nanoparticles in the present embodiment was 2.0 mg/mL, and ultrasonic dispersion was performed for 20 minutes.
(2) 0.1-5.0 mg/mL DMF solution of OT-1 was prepared. In the present embodiment, the concentration of OT-1 was 2.0 mg/mL.
(3) The OT-1 solution and the metal aluminum nanoparticle solution were mixed according to the volume of 1:1, after ultrasonic dispersion for half an hour, the reaction solution was transferred to a shaker, and shaked at room temperature at 320 rpm for 12 hours. After stopping shaking, the reaction solution was centrifuged at 6000 rpm/min for 10 minutes, and the supernatant was removed and the samples was lyophilized to remove the remaining small amount of solvent.

Embodiment 8

The vaccine 147.14 nm Al-Tert was prepared by mixing 147.14 nm metal aluminum nanoparticles with polypeptide Tert (DI-27).

Except the following conditions, other operations and conditions in the present embodiment were the same as those in Embodiment 7:

2.0 mg/mL DMF solution of Tert (DI-27) was prepared and mixed with the metal aluminum nanoparticle solution.

Comparative Embodiment 1

A vaccine (nano $Al(OH)_3$-OVA) was prepared by mixing aluminum hydroxide nanoparticles with OVA.

The preparation method of aluminum hydroxide nanoparticles was as follows: in a 20 mL small white flask, 5 mL of 3.6 mg/mL aluminum chloride hexahydrate $AlCl_3 \cdot 6H_2O$ and 5 mL of 0.04 M NaOH solution were added successively, and then the pH of the reaction solution was adjusted with 0.01 M NaOH to 7. After the mixture was stirred at room temperature for 20 minutes, the mixture was centrifuged at 8000 rpm to remove the supernatant. After the residue was washed twice with ultrapure water, dried under reduced pressure, and DMF was added to prepare a solution with a concentration of 2.0 mg/mL. The average particle size measured by TEM was 150.35±32.84 nm.

The preparation method of the vaccine nano $Al(OH)_3$-OVA was as follows: the aluminum hydroxide nanoparticles were mixed with OVA to prepare the vaccine, and other conditions were the same as those in Embodiment 3.

Comparative Embodiment 2

The vaccine ($Al(OH)_3$-OVA) was prepared by mixing commercial aluminum hydroxide gel adjuvant with OVA.

Specifically: the vaccine was prepared by mixing aluminum hydroxide gel adjuvant (purchased from Thermo Scientific, particle size was 4-10 μm) with OVA, and other conditions were the same as those in Embodiment 3.

Effect Embodiment 1 Humoral Immune Response

The lyophilized vaccines prepared in Embodiment 3, Comparative Embodiment 1, and Comparative Embodiment 2 were taken and their activities of stimulating humoral immune response were detected.

Experimental Conditions:

1. Animal Immunity:

7-week-old female $C_{57}BL/6$ mice were randomly divided into 5 groups with 3 mice in each group. Taking OVA as the antigen, the groups were 2.5 mg/mL OVA group, 10 mg/mL $Al(OH)_3$-OVA group, 10 mg/mL nano $Al(OH)_3$-OVA group, 10 mg/mL AlNPs-OVA group and control PBS group, respectively. The mice were immunized by subcutaneous injection of 100 μL each in the right inguinal area on the 0 th day and the 7 th day, respectively. On the 14 th day, the eyeballs were removed and serum was collected for IgG1 and IgG2a detection.

2. Preparation of Mouse Serum:

1) Removing the eyeball for blood collection: (1) the ears and the skin of the back of the neck of the mouse were grabbed with the thumb and index finger of the left hand, and the tail was fixed with the little finger; (2) the left forelimb of the mouse was pressed on the heart of the sternum with the middle finger, and the abdomen was pressed by the ring finger, then the thumb was twisted, and the eye skin on the blood side was gently pressed to make the eyeball congested and protrude; (3) the eyeball was taken with an elbow tweezer; (4) the thumb and index finger were twisted as needed to make the blood flow vertically into the centrifuge tube from the orbit at different speeds; (5) the left middle finger was simultaneously used to gently press the mouse heart to speed up the pumping speed of the heart; (6). when the blood was exhausted, the mouse was killed by dislocation.

2) Separation of serum: (1) the blood in the centrifuge tube was put at room temperature for 2 hours; (2) the blood was stored in a refrigerator at 4° C. for 3 hours; (3) after the blood had clotted and the clot had contracted, the mixture was centrifuged at 4000 rpm for 10 minutes; (4) the supernatant was taken in a clean EP tube and stored in a −80° C. refrigerator for later use.

3. Detection of Specific Antibody Subtype ELISA:

Referred to Mouse Anti-Ovalbumin IgG2a ELISA Kit, 96 tests, Quantitative Kit and Mouse Anti-Ovalbumin IgG1 ELISA Kit, 96 tests, Quantitative Kit produced by Alpha Diagnostic International, and detection was performed according to their instructions.

Figure 5:
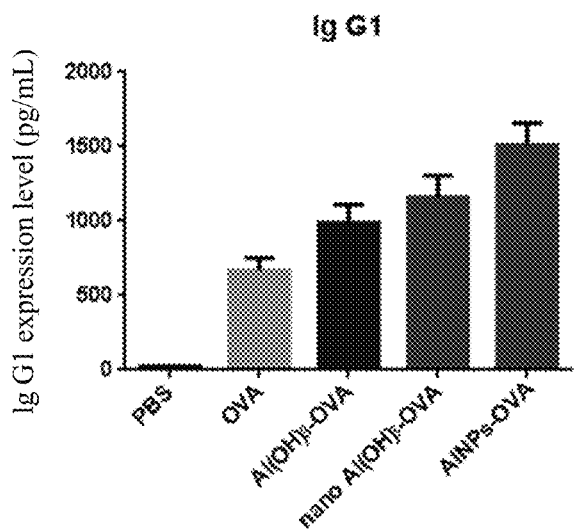
FIG. 5 is the titer of Th2 antibody subtype IgG1 induced by AlNPs-OVA in Effect Embodiment 1.
Figure 6:
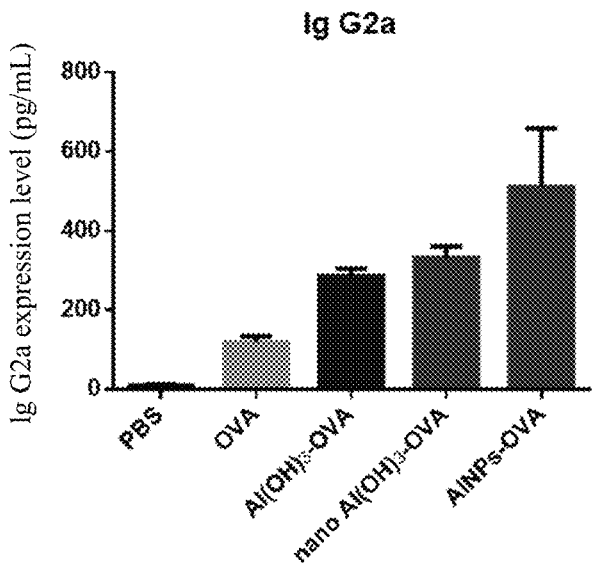
FIG. 6 is the titer of Th1 antibody subtype IgG2a induced by AlNPs-OVA in Effect Embodiment 1.

The specific experimental results could be found in Table 1, FIG. 5 and FIG. 6. Wherein, the antibody titer value was the OD 450 nm value measured by a microplate reader (EXL-800; Bio-Tek, Winooski, VT, USA).

TABLE 1

| Group | Th2 antibody subtype Ig G1 titer (pg/mL) | Th1 antibody subtype Ig G2a titer (pg/mL) |
|---|---|---|
| PBS | 20.062 ± 2.73 ** | 10.062 ± 2.73 ** |
| OVA | 669.9742 ± 84.47 ** | 119.9742 ± 13.76 * |
| $Al(OH)_3$-OVA | 987.2912 ± 123.58 * | 287.2912 ± 17.84 * |
| Nano $Al(OH)_3$-OVA | 1107.307 ± 77.11 * | 332.8065 ± 28.25 * |
| AlNPs-OVA | 1556.6 ± 83.54 | 566.5995 ± 69.39 |

Note:
* $P < 0.05$,
** $P < 0.01$, there were significant differences between the AlNPs-OVA group and the other four groups.

It can be seen from Table 1, FIG. 5 and FIG. 6 that:

the ability of AlNPs-OVA as a vaccine to induce the production of Th2 antibody subtype IgG1 and Th1 antibody subtype IgG2a is significantly higher than that of the other four groups.

Effect Embodiment 2 Cellular Immune Response

The lyophilized vaccines prepared in Embodiment 3, Comparative Embodiment 1, and Comparative Embodiment 2 were taken and their activities of stimulating cellular immune response were detected.

Experimental Conditions:

1. Animal Immunity:

7-week-old female $C_{57}BL/6$ mice were randomly divided into 5 groups with 2 mice in each group. Taking OVA as the antigen, the groups were 2.5 mg/mL OVA group, 10 mg/mL $Al(OH)_3$-OVA group, 10 mg/mL nano $Al(OH)_3$-OVA group, 10 mg/mL AlNPs-OVA group and control PBS group. The mice were immunized by subcutaneous injection of 100 μL each in the right inguinal area on the 0 th day and the 7 th day, respectively. On the 14 th day, the mice were sacrificed by cervical dislocation, and the spleen and draining lymph nodes were collected for flow cytometry.

2. Preparation of Mouse Spleen Cells

1) The mice were sacrificed by cervical dislocation, and the spleen was taken into a 60 mm dish containing 5 mL of PBS, then the spleen was ground to disperse cells, then filtered into a 15 mL centrifuge tube through a 200 mesh filter, then centrifuged at 1200 rpm at 4° C. for 5 min, and the supernatant was discarded;

2) 1 mL of red blood cell lysate was added, and the mixture was stood at 4° C. for 15 min and shaked every 5 min, then 10 mL of PBS was added to terminate, then the mixture was centrifuged at 1200 rpm at 4° C. for 5 min; the supernatant was discarded, and the spleen cells were resuspended in 1 mL of FACS and counted.

3. Preparation of Draining Lymph Nodes of Mice

Mice were sacrificed by cervical dislocation, and the right inguinal lymph nodes were taken into a 60 mm dish containing 5 mL of PBS, grounded to disperse cells, then filtered into a 15 mL centrifuge tube through a 200 mesh filter, then centrifuged at 1200 rpm at 4° C. for 5 min, and the supernatant was discarded, then lymph node cells were resuspended in 1 mL of FACS (FACS referred to a PBS solution containing 0.1% bovine serum albumin) and counted.

4. Detection of Antigen-Specific T Lymph Node Cells by Flow Cytometry $1×10^6$ spleen/lymph node cells were taken into a flow tube, and CD45-Pacific Blue, CD3-PE-Dazzle-594, CD4-BV421, CD8-PE-Cy5, CD19-BV650, CD11c-APC-Cy7, CD11b-BV711, Anti-SIINFEKL-H-2kb-PE were flow antibody stained (the above antibodies were purchased from BD Company (Becton, Dickinson and Company) in the United States), stained at 4° C. for 30 min in the dark, and 3 mL of FACS (FACS referred to PBS solution containing 0.1% bovine serum albumin) was added, then the mixture was centrifuged at 1200 rpm for 5 min at 4° C.; the supernatant was discarded, and the cells were vortexed to resuspend, and detected by Cytek Aurora flow analyzer.

Figure 7:
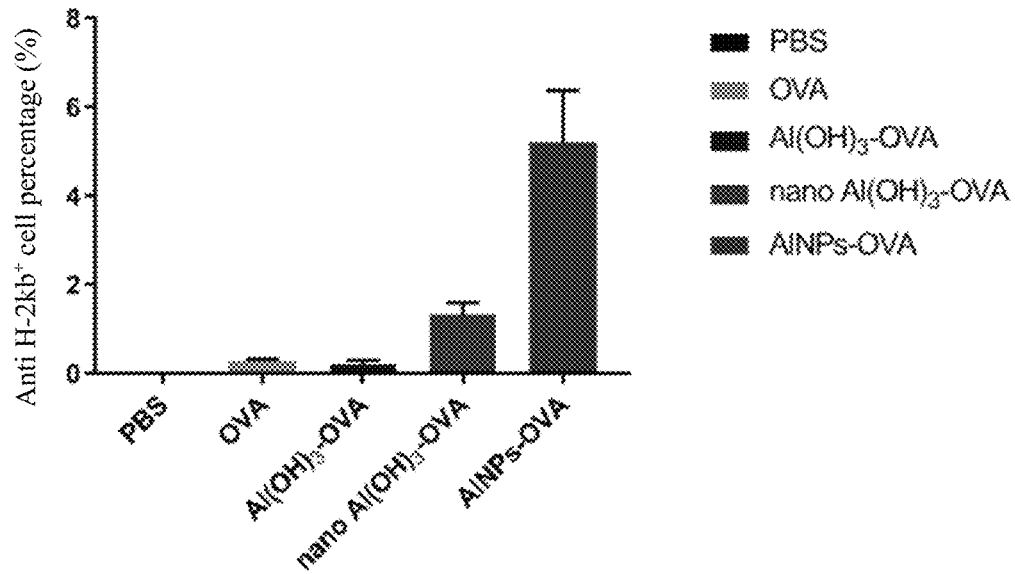
FIG. 7 is the percentage of the number of antigen-specific T cells in draining lymph node cells induced by AlNPs-OVA in Effect Embodiment 2.
Figure 8:
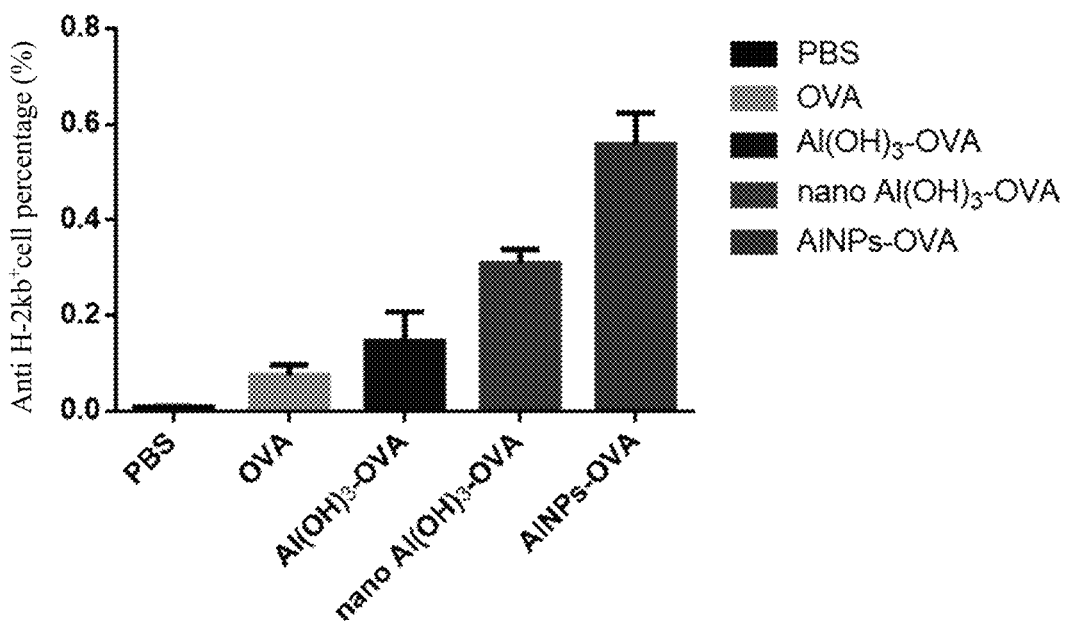
FIG. 8 is the percentage of the number of antigen-specific T cells in spleen cells induced by AlNPs-OVA in Effect Embodiment 2.

The specific experimental results could be found in Table 2-3, FIG. 7 and FIG. 8. Wherein, the percentage of the number of antigen-specific T cells was obtained by applying Flowjo software to analyze the data after Cytek Aurora flow analyzer detection, and the result was the percentage of the number of cells.

TABLE 2

Counts of spleen cells and draining lymph node cells in mice

| Group | Draining lymph node cells/ $1 × 10^6$ cells | Spleen cells/ $1 × 10^6$ cells |
|---|---|---|
| PBS | 1.85 ± 0.28 | 74.00 ± 9.19 |
| OVA | 2.76 ± 0.83 | 69.5 ± 10.61 |
| $Al(OH)_3$-OVA | 8.61 ± 2.25 | 151.75 ± 34.29 |
| Nano $Al(OH)_3$-OVA | 1.70 ± 0.78 | 133.5 ± 45.25 |
| AlNPs-OVA | 13.65 ± 2.65 | 109.75 ± 8.84 |

It can be seen from Table 2 that the ability of AlNPs-OVA as a vaccine to induce the production of spleen cells and draining lymph node cells is significantly higher than that of the other four groups.

TABLE 3

Percentage of antigen-specific T cells in draining lymph node cells and spleen cells of mice

| Group | Percentage of antigen-specific T cells in draining lymph node cells/% | Percentage of antigen-specific T cells in spleen cells/% |
|---|---|---|
| PBS | 0 * | 0.009 ± 0 ** |
| OVA | 0.3 ± 0.03 * | 0.075 ± 0.02 * |
| $Al(OH)_3$-OVA | 0.225 ± 0.09 * | 0.145 ± 0.06 * |
| Nano $Al(OH)_3$-OVA | 1.325 ± 0.28 * | 0.31 ± 0.03 * |
| AlNPs-OVA | 5.21 ± 1.17 | 0.559 ± 0.07 |

Note:
* $P < 0.05$,
** $P < 0.01$, there were significant differences between the AlNPs-OVA group and the other four groups.

It can be seen from Table 3, FIG. 7 and FIG. 8 that the ability of AlNPs-OVA as a vaccine to induce the production of antigen-specific T lymph node cells is significantly higher than that of the other four groups.

Effect Embodiment 3

The lyophilized vaccines prepared in Embodiment 4 and Embodiment 5 were taken and their activities of stimulating immune response were detected.

Experimental Conditions:

Female $C_{57}BL/6$ mice, 8-week-old, were purchased from Beijing Vital River Company;

the mice were randomly divided into 5 groups with 4 mice in each group, and the groups were PBS group, OVA protein group (160 μg OVA/mouse), metal aluminum nanoparticle group (1 mg/mouse, wherein, 1 mg of metal aluminum nanoparticles were composed of 0.5 mg 287.82 nm Al and 0.5 mg 147.14 nm Al), 287.82 nm Al-OVA group (1 mg Al/160 μg OVA/mouse) and 147.14 nm Al-OVA group (1 mg Al/160 μg OVA/mouse), respectively.

On the 0 th and 7 th day, mice were immunized by intradermal injection on the left back, 100 μL/mouse/time.

On the 14 th day, $5'10^5$ B16F10 cells/mouse were subcutaneously inoculated on the right back of the mice.

The tumor was measured every 2 days from the 21 st day, and the tumor volume=length×width×width/2.

Figure 9:
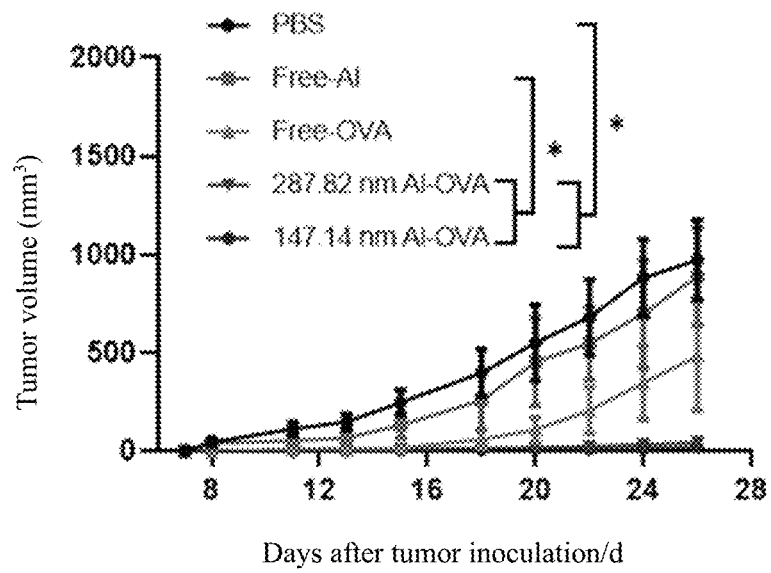
FIG. 9 is the preventive effect of Al-OVA on tumor growth in Effect Embodiment 3.

The specific experimental results could be seen in Table 4 and FIG. 9.

TABLE 4

| Group | Days after tumor inoculation/d | Tumor volume/mm³ |
|---|---|---|
| PBS | 26 | 974.15 ± 351.57 |
| OVA (Free-OVA) | 26 | 886.91 ± 431.86 |
| Metal aluminum nanoparticles (Free-Al) | 26 | 551.36 ± 481.76 |
| 287.82 nm Al-OVA | 26 | 44.71 ± 18.16* |
| 147.14 nm Al-OVA | 26 | 21.63 ± 15.58* |

Note:
*$P < 0.05$, there were significant difference between the 147.14 nm Al-OVA group, the PBS group and the Free-Al group, and there were significant difference between the 287.82 nm Al-OVA group, the PBS group and the Free-Al group.

It can be seen from Table 4 and FIG. 9 that the metal aluminum nano-protein vaccine can significantly slow down the tumor growth in mice, and the preventive effect is better than the other three groups.

Effect Embodiment 4

The lyophilized vaccines prepared in Embodiment 5 and Comparative Embodiment 2 were taken and their activities of stimulating immune response were detected.
Experimental conditions:
Female $C_{57}BL/6$ mice, 8-week-old, were purchased from Beijing Vital River Company;
on the 0 th day, $1 \times 10^6$ B16F10 cells/mouse were subcutaneously inoculated on the right back of the mice.
The mice were randomly divided into 4 groups with 2 mice in each group, and the groups were PBS group, OVA protein group (100 μg OVA/mouse), commercial aluminum hydroxide gel group (1.332 mg Al $(OH)_3$/100 μg OVA/mouse) and 147.14 nm Al-OVA group (0.23 mg Al/100 μg OVA/mouse), respectively.
On the 7th day, the mice were immunized by subcutaneous injection on the right groin, once every 3 days, a total of 6 times, 100 μL/mouse/time.
The tumor was measured every 2 days from the 7 th day, and the tumor volume=length×width×width/2.
The specific experimental results could be seen in Table 5 and FIG. 10.

TABLE 5

| Group | Days after tumor inoculation/d | Tumor volume/mm³ |
|---|---|---|
| PBS | 16 | 727.47 ± 132.65 |
| OVA (Free-OVA) | 16 | 467.39 ± 88.51 |
| Al(OH)₃-OVA | 16 | 144.50 ± 31.94** |
| 147.14 nm Al-OVA | 16 | 37.75 ± 16.91** |

Note:
**$P < 0.01$, there were significant difference between the 147.14 nm Al-OVA group, the PBS group and the Free-OVA group, and there were significant difference between the Al(OH)₃-OVA group and the PBS group.

Figure 10:
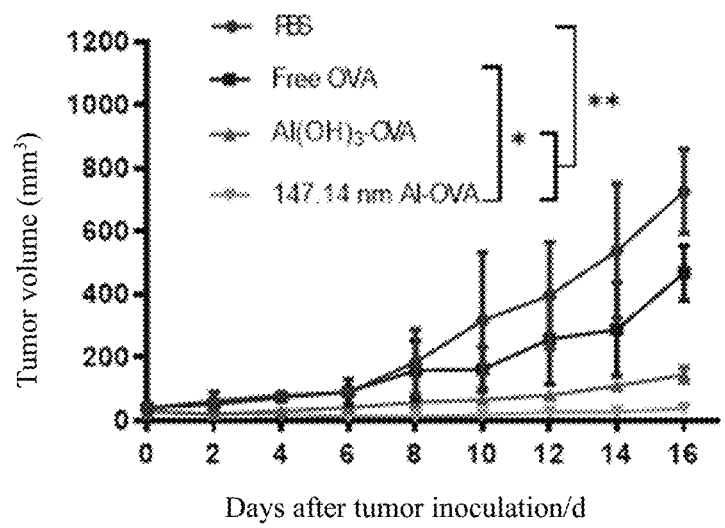
FIG. 10 is the therapeutic effect of Al-OVA on tumor growth in Effect Embodiment 4.

It can be seen from Table 5 and FIG. 10 that the metal aluminum nano-protein vaccine can significantly slow down the tumor growth in mice, and the therapeutic effect is better than the other three groups.

Effect Embodiment 5

The lyophilized vaccines prepared in Embodiment 7 and Comparative Embodiment 2 were taken and their activities of stimulating immune response were detected.
Experimental Conditions:
Female C57BL/6 mice, 8-week-old, were purchased from Beijing Vital River Company;
The mice were randomly divided into 5 groups with 3 mice in each group, and the groups were PBS group, 147.14 nm Al group (0.8 mg/mouse), OT1 short peptide group (50 μg OT1/mouse), and commercial aluminum hydroxide gel group (0.8 mg Al $(OH)_3$/50 μg OT1/mouse), 147.14 nm Al-OVA group (0.8 mg Al/50 μg OVA/mouse).
On the 0 th and 7 th day, mice were immunized by subcutaneous injection in the right groin, 100 μL/mouse/time.
On the 14 th day, $1 \times 10^6$ B16F10 cells/mouse were subcutaneously inoculated on the right back of the mice.
The tumor was measured every 2 days from the 25 th day, and the tumor volume=length×width×width/2.
The specific experimental results could be seen in Table 6 and FIG. 11.

TABLE 6

| Group | Days after tumor inoculation/d | Tumor volume/mm³ |
|---|---|---|
| PBS | 15 | 1106.10 ± 316.53 |
| OT1 (Free- OT1) | 15 | 719.39 ± 129.69* |
| Metal aluminum nanoparticles (Free-Al) | 15 | 634.86 ± 114.94 |
| Al(OH)₃-OT1 | 15 | 603.98 ± 154.92* |
| 147.14 nm Al-OT1 | 15 | 255.50 ± 73.32*** |

Note:
*$P < 0.05$,
***$P < 0.001$, there were significant difference between the 147.14 nm Al-OT1 group, the PBS group and the Free-Al group, and there were significant difference between the Al(OH)₃-OT1 group and the PBS group, and there were significant difference between the OT1 (Free-OT1) group and the PBS group.

Figure 11:
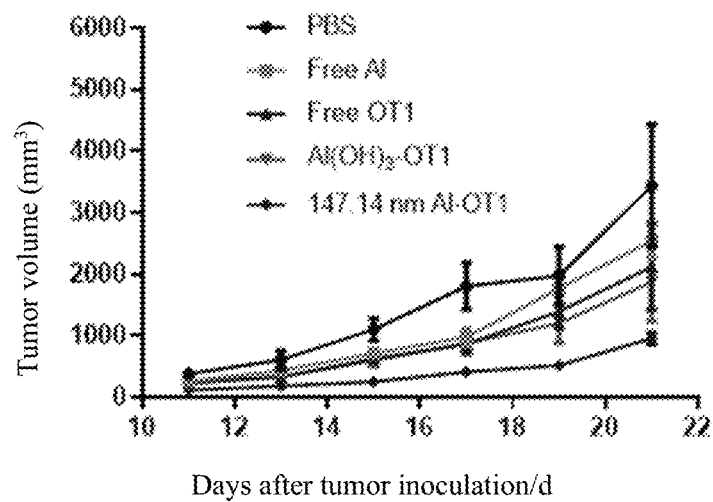
FIG. 11 is the preventive effect of Al-OT-1 on tumor growth in Effect Embodiment 5.

It can be seen from Table 6 and FIG. 11 that the metal aluminum nano-short peptide vaccine can slow down the tumor growth in mice, and the tumor volume is smaller than that of the other four groups.

Effect Embodiment 6

The lyophilized vaccine prepared in Embodiment 8 was taken and its activity of stimulating immune response was detected.
Experimental Conditions:
Female $C_{57}BL/6$ mice, 8-week-old, were purchased from Beijing Vital River Company;
the mice were randomly divided into 4 groups with 3 mice in each group, and the groups were PBS group, 147.14 nm Al group (2.5 mg Al/mouse), Tert (DI-27) polypeptide group (250 μg Tert (DI-27)/mouse) and 147.14 nm Al-Tert (DI-27) group (2.5 mg Al/250 μg Tert (DI-27)/mouse).
On the 0 th and 7 th day, mice were immunized by subcutaneous injection in the right groin, 100 μL/mouse/time.
On the 14 th day, $5 \times 10^5$ B16F10 cells/mouse were subcutaneously inoculated on the right back of the mice.
The tumor was measured every 2 days from the 21 st day, and the tumor volume=length×width×width/2.
The specific experimental results could be seen in Table 7 and FIG. 12.

TABLE 7

| Group | Days after tumor inoculation/d | Tumor volume/mm³ |
|---|---|---|
| PBS | 21 | 748.43 ± 159.59 |
| Metal aluminum nanoparticles (Free-Al) | 21 | 722.58 ± 97.72 |
| Tert (Free-Tert) | 21 | 604.92 ± 167.18 |
| 147.14 nm Al-Tert | 21 | 134.49 ± 38.63** |

Note:
**$P < 0.01$, there were significant difference between the 147.14 nm Al-Tert group, the PBS group, the Free-Al group and the Tert (Free-Tert) group.

Figure 12:
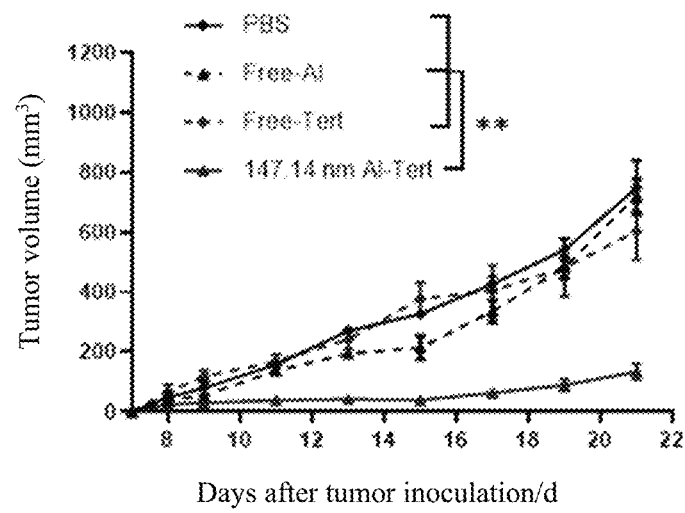
FIG. 12 is the preventive effect of Al-Tert on tumor growth in Effect Embodiment 6.

It can be seen from Table 7 and FIG. 12 that the metal aluminum nano-polypeptide vaccine can significantly slow down the tumor growth in mice, and the preventive effect is better than that of the other three groups.

What is claimed is:

1. A vaccine composition, wherein, the vaccine composition comprises the vaccine adjuvant, and an antigen or DNA encoding the antigen; wherein the vaccine adjuvant comprises metal aluminum nanoparticles, wherein the average particle size of the metal aluminum nanoparticles is 10-1000 nm, and wherein the metal aluminum nanoparticles are composed of a metal aluminum core with zero valent aluminum ($Al^0$) and amorphous alumina layer with a thickness of 3-5 nm on the surface.

2. The vaccine composition as defined in claim 1, wherein the antigen is one or more of short peptides, polypeptides and proteins.

3. The vaccine composition as defined in claim 2, wherein, the short peptide is antigen peptide OT-1 of ovalbumin OVA, antigenic glycoprotein gp100 of melanoma cells or apoptosis inhibitory protein survivin/birc5-1;
   or, the polypeptide is telomerase activity catalytic unit TERT, or, "T cell recognition melanoma antigen MART-1, MOG35-55, PADRE, Trp2 or survivin/birc5-2";
   or, the protein is ovalbumin OVA;
   or, the mass ratio of the metal aluminum nanoparticles to the antigen is 2:(0.1-10).

4. The vaccine composition as defined in claim 3, wherein, sequence of the antigenic peptide OT-1 is shown in SEQ ID NO: 1; molecular weight of the antigenic peptide OT-1 is 963.14 g/mol;
   or, sequence of the TERT is shown in SEQ ID NO: 2; molecular weight of the TERT is 3046.70 g/mol;
   or, molecular weight of the OVA is 298.4 g/mol;
   or, the mass ratio of the metal aluminum nanoparticles to the antigen is 2:3 or 1:1.

5. The vaccine composition as defined in claim 1, where the average particle size of the metal aluminum nanoparticles is 10-300 nm,
   or, the metal aluminum nanoparticles are metal aluminum nanoparticles with a dispersion coefficient of circumscribed circle diameter≤0.21.

6. The vaccine composition as defined in claim 1, wherein, the average particle size of the metal aluminum nanoparticles is 88.85 nm±8.86 nm, 147.14 nm±11.95 nm, 139.76±42.81 nm or 287.82 nm±24.13 nm.

7. The vaccine composition as defined in claim 1, wherein, the metal aluminum nanoparticles are prepared by electric explosion method or ligand regulation method.

8. The vaccine composition as defined in claim 7, wherein, the electric explosion method comprises the following steps: in an inert environment, vaporizing the aluminum wire by electric current to form aluminum vapor, and after condensation, obtaining the metal aluminum nanoparticles;
   or, the ligand regulation method comprises the following steps: in an atmosphere with a water content lower than 10 ppm and an oxygen content lower than 100 ppm, in the presence of titanium catalyst, reacting the ligand solution with the precursor solution; the ligand is a polymer with a functional group containing sulfur atom as a terminal group, and the polymerization degree of the ligand is 10-1000; the structural formula of the precursor is $H_3Al-X$, and the X is an organic molecule, and the organic molecule contains atoms that are able to coordinate with aluminum and have lone pair electrons.

9. The vaccine composition as defined in claim 7, wherein, in the ligand regulation method, the titanium catalyst is titanium tetraisopropanolate;

or, in the ligand regulation method, the ligand is

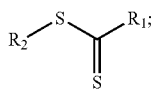

wherein: $R^1$ is $C_{1-10}$ alkyl, $C_{6-30}$ aryl, or $C_{6-30}$ aryl substituted by $R^{1a}$; $R^2$ is

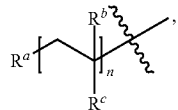

$R^a$ is $C_{1-10}$ alkyl, or $C_{1-10}$ alkyl substituted by $R^{a1}$, $R^{a1}$ is $C_{6-30}$ aryl; $R^b$ is H or $C_{1-10}$ alkyl; $R^C$ is $C_{6-30}$ aryl, $C_{6-30}$ aryl substituted by $R^{c1}$, or

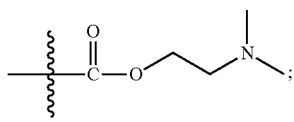 [SMILES: *C(=O)OCCN(C)C]

$R^{1a}$ and $R^{c1}$ are each independently $C_{1-10}$ alkyl or halogen;
or, in the ligand regulation method, the polymerization degree of the ligand is 20-1000;
or, in the ligand regulation method, the PDI of the ligand is 1-2;
or, in the ligand regulation method, the structural formula of the ligand is shown in formula (1), wherein Mn is 4.5 kg/mol, n is 42, and PDI is 1.09;

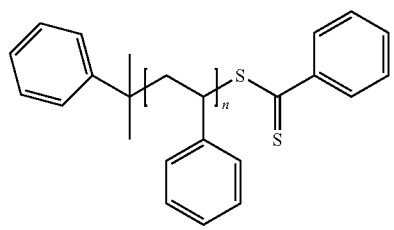

formula (1)

or, in the ligand regulation method, in the precursor, X is an organic molecule containing N or O atoms;
or, in the ligand regulation method, in the reaction solution, the concentration of the precursor is 15-500 mM;
or, in the ligand regulation method, the molar ratio of the ligand to the precursor is 3:(500-800);
or, in the ligand regulation method, the molar ratio of the titanium catalyst to the precursor is 1:(350-550);
or, in the ligand regulation method, the molar ratio of the ligand, the precursor and the titanium catalyst is 1:(60-520):(0.04-1.6);
or, in the ligand regulation method, the solvent in the ligand solution and the precursor solution is an aprotic solvent.

10. The vaccine composition as defined in claim 9, wherein, in the ligand regulation method, the polymerization degree of the ligand is 40-240;
or, in the ligand regulation method, the PDI of the ligand is 1-1.51;
or, in the ligand regulation method, in the precursor, X is tertiary amine or tetrahydrofuran;
or, in the ligand regulation method, in the reaction solution, the concentration of the precursor is 20-100 mM;
or, in the ligand regulation method, the molar ratio of the ligand to the precursor is 3:800;
or, in the ligand regulation method, the molar ratio of the titanium catalyst to the precursor is 1:400;
or, in the ligand regulation method, the molar ratio of the ligand, the precursor and the titanium catalyst is 1:(70-500):(0.05-1.5);
or, in the ligand regulation method, the solvent in the ligand solution and the precursor solution is one or more of toluene, tetrahydrofuran and ether solvents.

11. The vaccine composition as defined in claim 1, wherein, a preparation method of the vaccine adjuvant comprises the following steps: mixing the metal aluminum nanoparticles with solvent A to prepare a vaccine adjuvant suspension.

12. The vaccine composition as defined in claim 11, wherein, the solvent A is one or more of alcohol solvents, ether solvents, ketone solvents, dimethyl sulfoxide, N,N-dimethylformamide and tetrahydrofuran;
or, in the vaccine adjuvant suspension, the concentration of the metal aluminum nanoparticles is 0.1-100 mg/ml;
or, the mixing method is ultrasonic dispersion.

13. A lyophilized vaccine, wherein, the lyophilized vaccine comprises metal aluminum nanoparticles and antigens, wherein the average particle size of the metal aluminum nanoparticles is 10-1000 nm, wherein the metal aluminum nanoparticles are composed of a metal aluminum core with zero valent aluminum ($Al^0$) and amorphous alumina layer with a thickness of 3-5 nm on the surface, and wherein the antigens is one or more of short peptides, polypeptides and proteins.

14. A preparation method of the vaccine composition as defined in claim 1, wherein, the preparation method comprises the following steps: mixing the vaccine adjuvant with a solution containing the antigen, and carrying out an incubation reaction.

15. The preparation method of the vaccine composition as defined in claim 14, wherein, the solution containing the antigen is prepared by the following method: mixing the antigen with solvent B.

16. The preparation method of the vaccine composition as defined in claim 15, wherein, the solvent B is water, PBS buffer, DMF or alcohol solvent;
or, in the solution containing the antigen, the concentration of the antigen is 10 mg/ml;
or, when the vaccine adjuvant in the form of the vaccine adjuvant suspension is mixed with the solution containing the antigen, the solvent A and the solvent B are soluble;
or, the incubation reaction is carried out according to the following steps: carrying out ultrasonic dispersion first, followed by incubation;
or, the incubation reaction is carried out under the condition of 80-800 rpm;
or, the time of the incubation reaction is 1-24 hours;
or, after the incubation reaction, the vaccine composition is centrifuged to remove supernatant.

17. The lyophilized vaccine as defined in claim 13, wherein, the lyophilized vaccine is prepared by the following method: mixing the vaccine composition with water and lyophilizing;

the vaccine composition comprises the vaccine adjuvant, and an antigen or DNA encoding the antigen, and the vaccine adjuvant comprises metal aluminum nanoparticles.

18. A method for enhancing a humoral or cellular immune response comprising administering to a subject in need thereof metal aluminum nanoparticles and a vaccine; wherein the average particle size of the metal aluminum nanoparticles is 10-1000 nm, and wherein the metal aluminum nanoparticles are composed of a metal aluminum core with zero valent aluminum ($Al^0$) and amorphous alumina layer with a thickness of 3-5 nm on the surface.

* * * * *

```
                        SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: antigenic peptide OT-1

<400> SEQUENCE: 1

Ser Ile Ile Asn Phe Glu Lys Leu
1               5

<210> SEQ ID NO 2
<211> LENGTH: 27
<212> TYPE: PRT
<213> ORGANISM: Artificial Sequence
<220> FEATURE:
<223> OTHER INFORMATION: telomerase activity catalytic unit TERT

<400> SEQUENCE: 2

Asp Leu Gln Pro Tyr Met Gly Gln Phe Leu Lys His Leu Gln Asp Ser
1               5                   10                  15

Asp Ala Ser Ala Leu Arg Asn Ser Val Val Ile
            20                  25
```